US006146384A

United States Patent [19]

Lee et al.

[11] Patent Number: 6,146,384

[45] Date of Patent: *Nov. 14, 2000

[54] ORTHOPEDIC FIXATION DEVICE AND METHOD OF IMPLANTATION

[75] Inventors: Casey K. Lee, Short Hills, N.J.; Robert A. Farris, Memphis, Tenn.; Bradley I. Coates, Rossville, Tenn.; Michael C. Sherman, Memphis, Tenn.

[73] Assignee: SDGI Holdings, Inc., Wilmington, Del.

[ * ] Notice: Under 35 U.S.C. 154(b), the term of this patent shall be extended for 536 days.

[21] Appl. No.: 08/542,603

[22] Filed: Oct. 13, 1995

[51] Int. Cl.[7] .......... A61B 17/68

[52] U.S. Cl. .......... 606/73; 606/69; 606/72; 606/60

[58] Field of Search .......... 606/60, 65, 69, 606/70, 72, 73; 411/84, 85, 107, 409, 551

[56] References Cited

U.S. PATENT DOCUMENTS

| | | | |
|---|---|---|---|
| 2,379,752 | 7/1945 | Schultz | 403/299 |
| 2,485,531 | 10/1949 | Dzus et al. | 606/73 |
| 4,711,234 | 12/1987 | Vives et al. . | |
| 4,716,893 | 1/1988 | Fischer et al. . | |
| 4,850,063 | 7/1989 | Abbate | 4/252.1 |
| 4,854,311 | 8/1989 | Steffee | 606/66 |
| 5,059,193 | 10/1991 | Kuslich . | |
| 5,098,433 | 3/1992 | Freedland . | |
| 5,102,421 | 4/1992 | Anspach, Jr. . | |
| 5,133,719 | 7/1992 | Winston . | |
| 5,135,528 | 8/1992 | Winston . | |
| 5,167,665 | 12/1992 | McKinney . | |
| 5,209,753 | 5/1993 | Biedermann et al. . | |

FOREIGN PATENT DOCUMENTS

| | | |
|---|---|---|
| 3509417 | 9/1986 | United Kingdom . |

*Primary Examiner*—Michael Buiz
*Assistant Examiner*—David O. Reip
*Attorney, Agent, or Firm*—Woodard, Emhardt, Naughton, Moriarty & McNett

[57] ABSTRACT and methods for attaching an implant to bone are disclosed. In one embodiment, the device 10 includes an elongated stud 15 defining an engaging surface 16 and a foot 20 projecting outwardly from an end 18 of the stud 15. The foot 20 is receivable through an opening O in the cortical layer R of the bone B and includes an upper surface 21 for contacting an internal surface R' of the cortical layer R. A fastener 25 is provided for engaging the engaging surface 16 of the stud 15, having a surface 29 for bearing against the implant I to clamp the implant I to the bone B when the fastener 25 is engaged to the engaging surface 16 of the stud 15 and the foot 20 is received in the opening O. In another embodiment, the apparatus 30 includes a number of additional studs 31 which are extendable together through the opening O. A wedge 36 can be provided to clamp the multiple studs within the bone opening.

7 Claims, 4 Drawing Sheets

ORTHOPEDIC FIXATION DEVICE AND METHOD OF IMPLANTATION

FIELD OF THE INVENTION

The present invention broadly concerns devices for use in orthopedic implant systems, particularly those using bone plates for maintaining long bone segments or vertebrae in a desired relationship. More specifically, the invention concerns methods and devices for rigidly engaging orthopedic implants to bone.

BACKGROUND OF THE INVENTION

Internal fixation is indicated for many orthopedic conditions resulting from disease, injury or deformity. Spinal implant systems can be used to temporarily stabilize the spine and maintain certain vertebrae in rigid position relative to each other while awaiting solid fusions of segments of the spine. Most spinal implant systems include bone plates and spinal rods which are fixed to the spine with various devices, such as bone screws, bolts, wires and connectors.

Various orthopedic techniques and systems have been developed to engage a bone plate or other orthopedic implant securely to bone. Implants are sometimes press fitted between two cortical walls or attached to the bone with bone screws, including cancellous, cortical and bicortical screws, or various wires and cables, hooks, clamps and pins. Unfortunately, complications can develop with many of these fixation methods. For example, bone screws can loosen over time, pull out or thread themselves back out. The associated failure of the bone to provide adequate support for the screw threads is heightened in weaker bone, such as found in older rheumatoid and osteoporitic patients. Bone screw failures often require revision and replacement with a larger replacement screw. This is particularly problematic because often a larger screw cannot be used.

Bone screws have a further disadvantage for spinal applications in that they usually require bicortical placement for secure fixation. The tip of the screw which extends out of the opposite side of the bone can damage soft tissue structures leading to obvious complications. When the site of fixation is the vertebral column, bicortical placement of the screws risks spinal cord injury which can lead to paralysis.

Several devices have been developed in an attempt to answer the limitations of the bone screws. For example, surgical toggle bolt or molly bolt approaches have been used as disclosed in U.S. Pat. No. 2,485,531 to Dzus, U.S. Pat. No. 5,098,433 to Freedland and German Patent No. 3509-417A. In Freedland and Dzus, a pivoting member rotates into a position to anchor the fastener. In the German reference, the arms of the anchoring device are separated and pressed into contact as a screw is threaded through the center of the device. In spite of these efforts, toggle bolts have not presented a viable answer because installation is time consuming and requires the application of torque to the bone. Furthermore, toggle bolt removal is extremely difficult and can cause extensive damage to the bone.

U.S. Pat. No. 4,716,893 to Fisher discloses a bone anchor for fastening a screw into cancellous bone. An anchor sleeve is fitted into a bore formed in a bone. The anchor sleeve is expanded by the introduction of a threaded screw. The bore must have substantial depth in order to receive the anchor sleeve which may unfortunately place the device in close proximity to vital soft tissue structures. A similar approach is described in U.S. Pat. No. 5,209,753 to Biedermann et al. Biedermann discloses a bone screw which defines a longitudinal bore and a pair of slits. A shaft is screwed into the bore and engaged into a threaded bore in the movable tip of the screw. The tip includes an expander portion. After the screw is engaged to bone, the shaft is unscrewed toward the head of the screw pulling the expander portion into the slitted bore which in turn expands the threaded portion of the screw. One disadvantage of this approach is that a separate removable tool is required to engage the removable tip. Moreover, this device provides no means for controlling the expansion of the slitted bone screw within the bone.

Vives (U.S. Pat. No. 4,711,234) discloses a retention pin assembly for fixing a bone plate or other prosthesis on bone tissue. The assembly is composed of two half pins that are pressed into a bore. The pins are shaped so that they will spread progressively apart as the surface of the opposing pins slidingly engage. The resilient bending of the half pins forces them to press against the wall of a bore formed in the cortical region of the bone.

U.S. Pat. No. 5,167,665 to McKinney teaches attaching orthopedic implants to bone with blind rivets. The McKinney invention is advantageous in that bicortical placement of the fastener is not required. Also, the device does not require applying torque to the bone as is necessary for toggle bolts. However, this device does require the application of force to the cortex of bone to engage the rivets to the bone. This is accomplished with a rivet gun or other tool after a rivet has been placed in a drilled hole. The blind rivets are similar to the toggle bolt approach because the drilled hole must be enlarged if the rivets must be removed and replaced. The enlarged hole may then require a fastener which is too large to used in the particular location.

A need has remained for orthopedic fixation devices which provide rigid fixation of implants to bone, do not require bicortical placement and minimize the intrusion into the cancellous material of the bone during implantation. A need has also remained for improved systems which reduce the trauma to the bone to be instrumented and the surrounding tissues.

SUMMARY OF THE INVENTION

In accordance with one aspect of the invention, an apparatus is provided for attaching an implant to bone. The device includes an elongated stud configured to extend through the implant and defining an engaging surface at one end and a foot adjacent the opposite end projecting outwardly therefrom. The foot is receivable through an opening in the cortical layer of the bone and includes an upper surface for contacting the internal surface of the cortical layer when the foot is received through the opening. The invention also includes a fastener for engaging the engaging surface of the stud. The fastener has a surface for bearing against the implant such that the implant is clamped between the bone and the bearing surface of the fastener when the fastener is engaged to the outer surface of the stud and the foot is received in the opening formed through the cortical layer of the bone.

In another embodiment of the present invention, the fixation apparatus includes a stud that is formed from a plurality of longitudinal sections. Each of the longitudinal sections defines an engaging surface and a driving face. A foot is formed on each longitudinal section and projects outwardly therefrom. The longitudinal sections are extendable together with the driving faces adjacent one another through the cortical opening. The foot of each of the plurality of longitudinal sections contact the underside of the cortical layer. A wedge and fastener arrangement engages the driving faces to firmly clamp the implant to the bone on the fixation apparatus.

The invention also contemplates methods for attaching an implant to bone which include: forming a cortical opening through the cortical layer of the bone; clearing a space in the cancellous tissue adjacent the cortical opening; positioning a fixation device through the opening, the device including a stud having an elongated portion extending through the cortical opening and an enlarged foot disposed within the space in the cancellous tissue; positioning the foot within the space to contact the cortical layer for preventing removal of the stud from the bone; disposing the implant against the bone at the cortical opening; and engaging the elongated portion of the stud to clamp the implant to the bone with the foot bearing against the underside of the cortical layer.

It is an object of the present invention to provide an improved orthopedic fixation device for affixing a bone plate or other orthopedic device to the bone of a patient.

It is a further object to provide such a fixation device that utilizes a minimum number of components that can be easily implanted and assembled.

Yet another object is realized by features of the invention that minimize the possibility of disassembly or loosening of the fixation device within the patient. Further objects and advantages of the present invention will be apparent from the following description.

DESCRIPTION OF THE PREFERRED EMBODIMENTS

Figure 1:
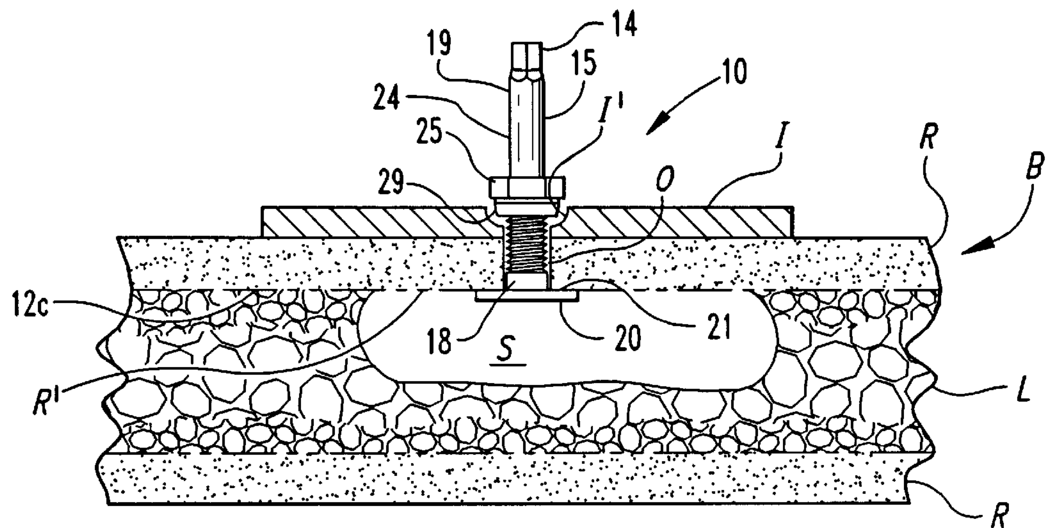
FIG. 1 is a side elevational view in partial cross-section of a device for attaching an implant to bone according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides methods and devices for attaching implants to bone. This invention can be used in any type of application where an implant must be affixed to bone, including, but not limited to, all areas of the spine, total hip and knee surgery, and elbow and shoulder replacement. The methods include creating an opening in the cortex, inserting an instrument into the opening and clearing a space free of cancellous bone. The device includes an elongated stud and a foot attached to an end of the stud. In one aspect of the invention, the foot is receivable through the opening in the cortex and can be rotated within the cleared space so that an upper surface of the foot contacts the cortical layer. The implant is then placed over the opening with the stud extending through the implant and a fastener is engaged to the stud. The fastener clamps the implant between the bone and the fastener with the foot bearing on the internal surface of the cortical bone. This invention is particularly advantageous because it provides rigid fixation of an implant to bone without bicortical placement of bone screws. This feature can reduce the risk of neuro-vascular injury and complications due to trauma to the surrounding soft tissues.

Figure 3:
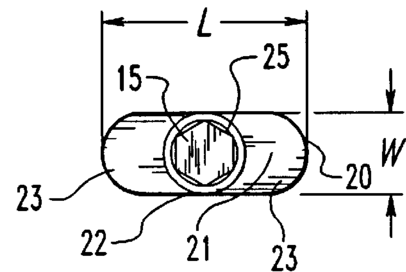
FIG. 3 is a top plan view of the orthopedic fixation device in FIG. 2.
Figure 2:
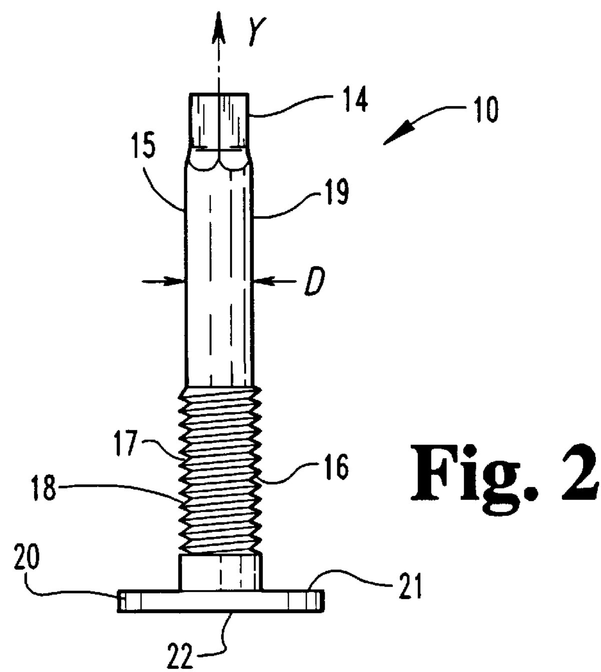
FIG. 2 is a side elevational view of the device in FIG. 1 with the fastener removed.

An orthopedic fixation device 10 for attaching an implant I to a bone B in accordance with a preferred embodiment of the present invention is depicted in FIGS. 1–3. The device 10 is shown in FIG. 1 inserted through an opening O in the cortical layer R of the bone B. The device 10 includes an elongated stud 15 defining an engaging surface 16 and having a first portion 18 and an opposite second portion 19 as shown more clearly in FIG. 2.

The device also includes a foot 20 adjacent the first portion 18 of the stud 15 and projecting outwardly therefrom. The foot 20 is configured to be receivable through the opening O in the cortical layer R of the bone B. The foot 20 has an upper surface 21 for contacting the underside or internal surface R' of the cortical layer R when the foot 20 is received through the opening O. The invention also contemplates fastener means for engaging the engaging surface 16 of the stud 15. In one particular embodiment, the fastener means includes an internally threaded nut 25 and a threaded portion 17 on the engaging surface 16 of the stud 15. As shown in FIG. 1, the fastener means, or nut 25 has a bearing surface 29 for bearing against the implant I to clamp the implant I between the bone B and the bearing surface 29 of the nut 25 when the nut 25 is engaged to the engaging surface 16 of the stud 15. Preferably, the bearing surface 29 is spherical to nest with a corresponding recess I' or scallop defined in the implant I. Engaging the fastener means also draws the upper surface 21 of the foot 20 into contact with the cortical layer R to firmly clamp the assembly together. Preferably, the second portion 19 of the stud 15 includes a hexagonal outer surface 14 disposed opposite of the foot 20. The hexagonal outer surface 14 is designed for receiving a tool, such as a wrench, to manipulate the stud 15 and rotate the foot 20 within the bone B.

Still referring to FIGS. 1–3, in one specific emdodiment, the foot 20 is integrally attached adjacent the first portion 18 of stud 15. The foot 20 is formed transverse to a centerline Y defined by stud 15. The foot 20 is elongated and has a length L that is greater than the width W. Preferably, the centerline Y intersects the foot 20 between its opposite ends 22. Most preferably, the intersection occurs midway 22 between the opposite ends 23 of foot 20. As shown in FIG. 3, the oppositely disposed ends 23 of the foot 20 preferably each have a semi-circular shape to facilitate atraumatic insertion through the bone opening O.

Figure 4:
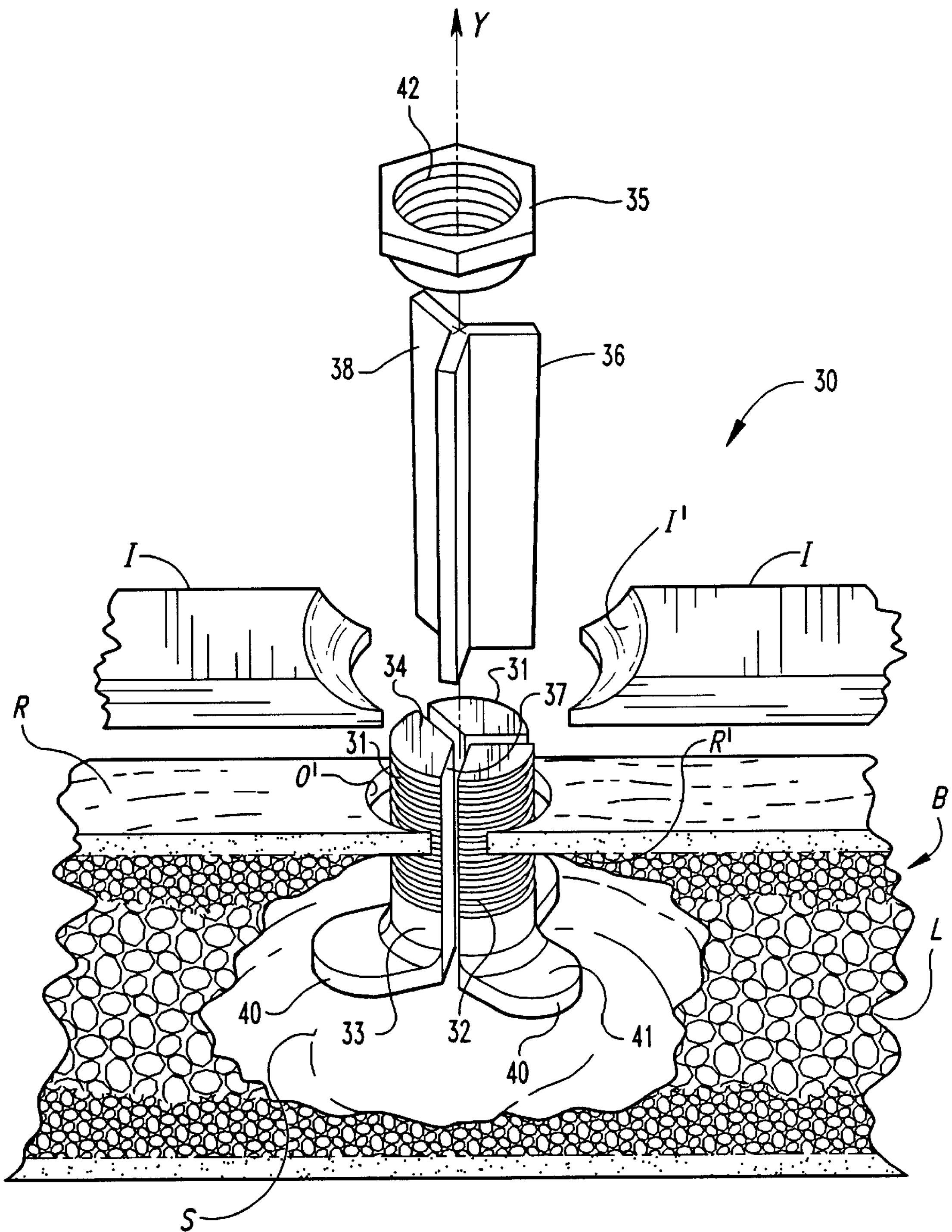
FIG. 4 is an exploded perspective view of a device according to another embodiment of the present invention.

Another embodiment of the present invention is shown in FIG. 4. In this embodiment, the device 30 includes a number of additional elongated studs 31 each defining an engaging surface 32 and having a first portion 33 and an opposite second portion 34. Each of the studs 31 are extendable together through the opening O. In one embodiment, a fastener 35 is simultaneously engageable to the engaging surface 32 of each of the studs 31. Preferably, the engaging surface 32 of each stud 31 is in the form of a portion of a cylinder so that the combination forms a complete cylinder. Each stud 31 includes a foot 40 adjacent the first portion 33 of each of the corresponding studs 31 which project outwardly therefrom. Each foot 40 is receivable through the opening O and has an upper surface 41 for contacting the internal surface R' of the cortical layer R as described above. Preferably, each foot is oriented transverse to a centerline defined by the corresponding stud. Most preferably, each foot is elongated, having a length that is greater than the width of the foot, although any suitable shape is contemplated.

Figure 5:
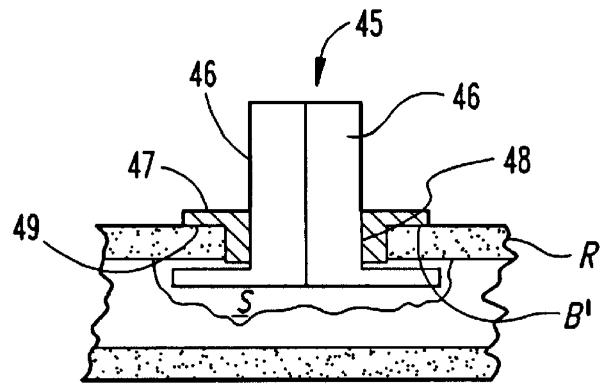
FIG. 5 is a side elevational view in partial cross-section of a device according to another embodiment of the present invention, which incorporates a collar to force the studs against each other.

In a preferred embodiment, the device 30 includes three studs 31. Other embodiments of this invention include any number of studs. For example, the use of two studs 46 is depicted in FIG. 5. The embodiments which provide a number of studs are advantageous because they allow for the insertion of the studs separately through the opening O formed in the cortical bone B, thereby minimizing the size required for the bone opening O.

In the embodiment shown in FIG. 4, the device also preferably includes a wedge 36 configured to be driven against at least one of the driving faces 37 of the plurality of studs 31 when the studs 31 extend through the opening O. The studs 31 are assembled within the bone opening with the driving faces 37 of the studs facing each other. The driving of the wedge 36 forces the studs 31 apart and against the inner surface O' of the opening O. Preferably, the wedge 36 includes a plurality of rectangular members 38 each configured to be driven against a corresponding one of the adjacent driving faces 37. As shown in FIG. 4, three rectangular members 38 of the wedge 36 correspond to the driving faces 37 of the studs 31.

Any appropriate means of engaging the engaging surfaces of the stud or studs is contemplated. For example, in FIG. 4, a nut 35 having internal threads 42 is simultaneously engageable to the externally threaded engaging surfaces 32 of each stud 31. For the device 45 illustrated in FIG. 5, the engaging surfaces 48 of the studs 46 are engaged with a collar 47. The collar 47 is preferably circular and defines an annular surface 49 for engaging a surface of the bone B'. The collar 47 is configured to be snugly received within the bone opening O and surround the engaging surfaces 48 of the studs 46.

Figure 6:
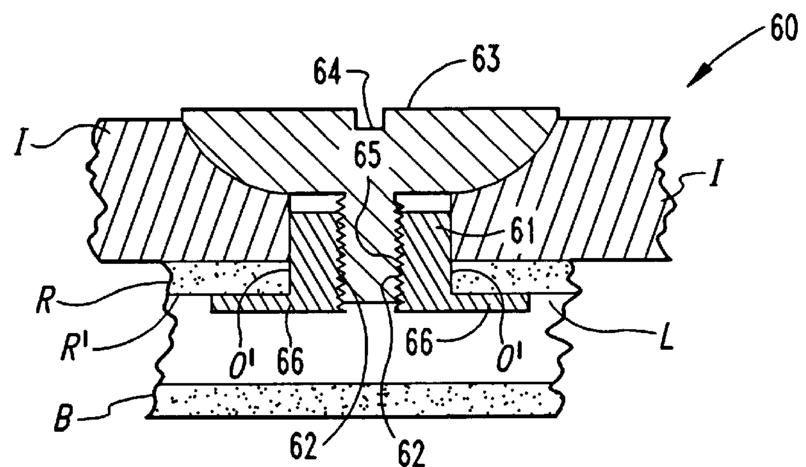
FIG. 6 is a side elevational view in partial cross-section of an orthopedic fixation device according to another embodiment of the present invention, which utilizes a screw to lock the device within an opening formed in a bone.

In FIG. 6 a device 60 according to a further embodiment is shown which includes a plurality of studs 61 having engaging surfaces 62 facing one another. A screw 63 engages the studs 61 internally at the engaging surfaces 62. The screw defines a driving notch 64 for receiving a driving tool and an external thread 65 that corresponds to the threaded engaging surfaces 62 of the studs 61. The torquing of the screw 63 pushes the studs 61 against the surface O' of the opening O and draws each foot 66 against the cortex R, thereby securing the implant I to the bone B.

Figure 7:
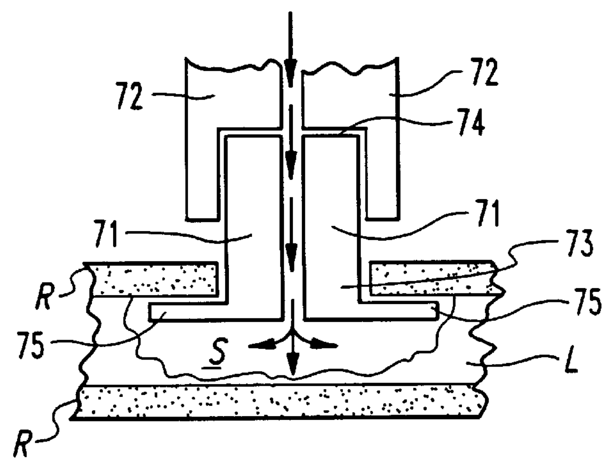
FIG. 7 is a side elevational view in partial cross-section depicting a method according to one aspect of the invention which includes introducing bone cement into the space formed in the cancellous tissue.

In one embodiment shown in FIG. 7, the invention also contemplates the use of a biocompatible cement which can be introduced into the space S within the bone. Bone cement is indicated for weakened bones such as in elderly rheumatoid or osteoporitic patients. Any suitable, biocompatible cement and method for delivering the cement to the space is contemplated. For example, in one method, a bone cement introducer 72 engages the second portion 74 of each of the studs 71 for delivering a quantity of cement into the cleared space S. In another specific embodiment, the cement is injected with a syringe. The cement surrounds the feet 75. This invention is advantageous because it allows easy and effective use of bone cement in a safe manner. Any contact with surrounding soft tissues is minimized or eliminated because the cement is confined to the space in the cancellous tissue. Fastener means or other elements to engage the engagement or driving surfaces of the studs 71 may then be employed as described above.

The present invention also includes methods for attaching an implant to bone. The methods can include steps of: exposing a bone to be instrumented; forming a cortical opening through the cortical layer of the bone to expose the cancellous tissue; clearing a space in the cancellous tissue adjacent the cortical opening; positioning a device through the opening, the device including a stud having an elongated portion extending through the cortical opening and an enlarged foot disposed within the space in the cancellous tissue; positioning the foot within the space to contact the cortical layer for preventing removal of the stud from the bone; disposing the implant against the bone at the cortical opening; and engaging the elongated portion of the stud to clamp the implant to the bone. This creates an internal surface of the cortical bone R for the foot to contact.

Figure 8:
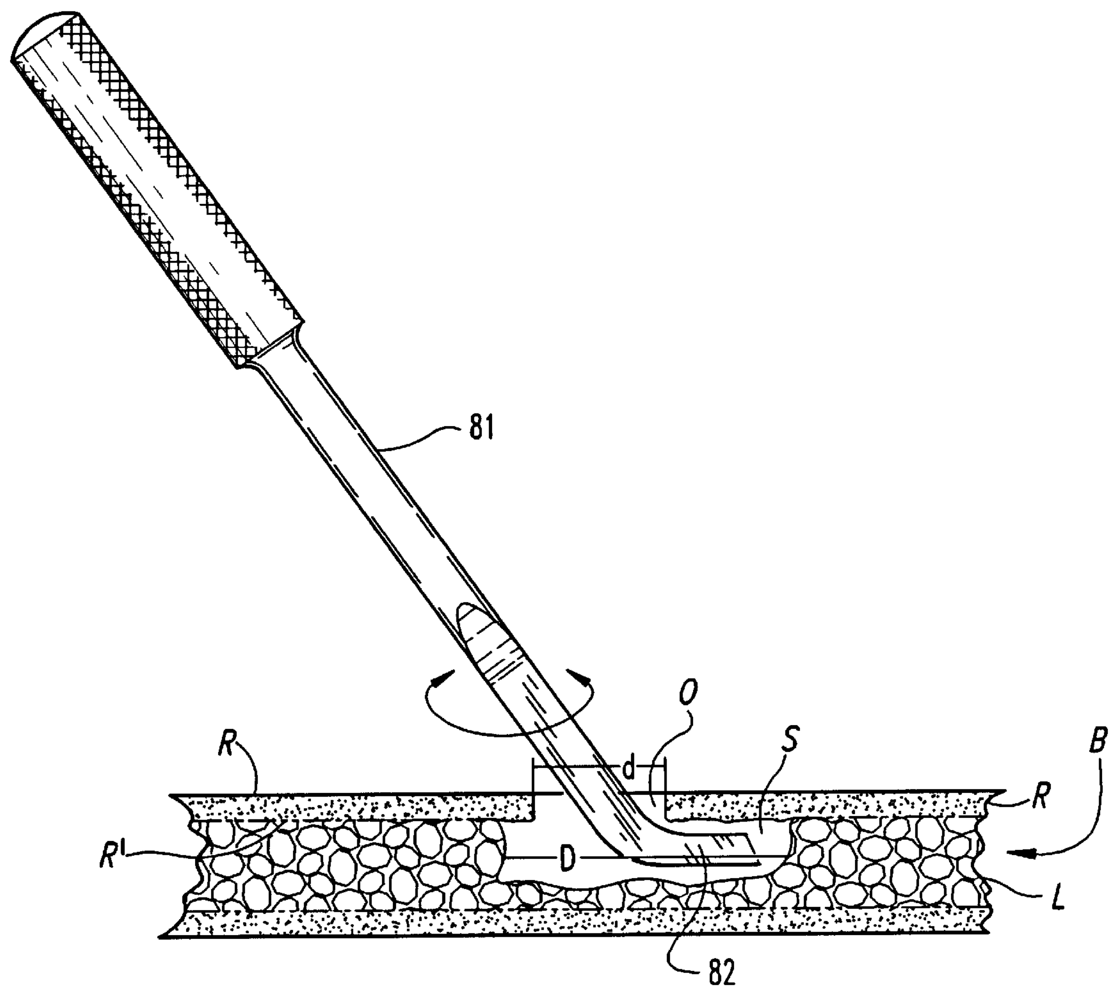
FIG. 8 is an illustrative side elevational view in partial cross-section depicting one method to form a space in cancellous bone material to prepare the bone to receive a fixation device in accordance with the present invention.

The bone is exposed according to appropriate surgical procedures. The cortical opening may be created by drilling a hole in the exposed bone. The clearing step may be accomplished in any suitable manner. In one specific embodiment of the invention, it is contemplated that a tool similar such as described by Winston (U.S. Pat. Nos. 5,133,719 and 5,135,528) may be used. Alternatively, a tool such as a Holt probe could be modified for this purpose. Referring to FIG. 8, an end of a Holt probe 81 could be bent to a hockey stick shape and the edge 82 sharpened for cutting. The probe is then rotated within the opening O to clear a space S in the cancellous tissue L. The diameter D of the space S is greater than the diameter d of the opening O and is preferably slightly larger than the effective diameter of the foot or feet of fixation devices disposed therein. Any tool which can be used to clear a space S in cancellous tissue L underneath the cortical bone R as shown in FIG. 8 is contemplated.

A device such as shown in FIG. 1 can then be positioned foot-first through opening O into the cancellous material L. The stud 17 is then rotated to orient the foot 20 transverse to the opening. In this specific embodiment, the bone opening O is formed in a shape similar to that of the foot 20. The stud is rotated within the bone, preferably through approximately 90°, so that the upper surface 21 of the foot 20 contacts the underside of the cortical bone R. Where the device as shown in FIG. 4 includes a plurality of elongated studs 31, each stud 31 can be individually positioned through the opening O to contact the cortical bone R from inside the space S. The use of multiple studs allows for the individual insertion of each stud which require a smaller opening. In this specific embodiment, the bone opening O can be generally circular.

Once the apparatus, such as devices 10 or 30, is positioned in the opening, the implant is disposed against the bone at the cortical opening. Preferably the stud 17 is disposed within an opening 28 defined in the implant I as shown in FIG. 1.

The engaging step includes employing any means which will clamp the implant to the bone. In one specific embodiment, a fastener is provided to engage the engaging portion of the stud or studs. For example, an internally threaded nut 25 can be threaded onto an externally threaded engaging portion 16 of stud 17 as shown in FIG. 1. Tightening the nut 25 onto stud 15 draws a bearing surface 29 of nut 25 against the outer surface of implant I. The final torquing of nut 25 draws the upper surface 21 of each foot 20 into contact with the inner surface R' of the cortical bone material, clamping the implant to the bone.

Alternatively, the engaging step may include inserting a wedge between driving faces of the studs such that the wedge and the studs fit snugly within the opening. The engaging step may also include applying a biocompatible bone cement to the space. It is also contemplated that the engaging means may include an internal screw.

Referring to FIG. 1, the excess portion 24 of the second end 19 of the stud 15 can be trimmed to reduce the profile of the system, once the engaging step is completed.

The devices of this invention are preferably formed of medical grade stainless steel, titanium, or any other biocompatible, high strength material. The devices can be provided in any size which is suitable to the particular patient, medical condition and body location. In a preferred embodiment, the stud is about one inch (2.5 cm) long with a diameter of ⅛ inch (4 mm). The foot of the same embodiment could be about 7/16 inch long (1 cm) and ⅛ inch wide (4 mm).

The present invention provides methods and devices for securely engaging implants to bone without bicortical screw placement. The complications due to soft tissue trauma and risk of neuro-vascular injury caused by bicortical screw placement are completely avoided. Because the devices of this invention rest in the cancellous bone just below the cortical level, pull-out strength is comparable to bone screws. Furthermore, backing out is impossible. This invention further addresses the limitations of bone screws because it can be used in revision situations, especially after removal of screws. For example, the devices of this invention can be used to obtain fixation in the already existing screw hole where larger bone screws would be needed but cannot be used.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. An orthopedic internal fixation system for maintaining bones in a desired spatial relationship, at least one of the bones having an opening formed through the cortical layer thereof, the system comprising:

a bone implant configured for supporting the bones in the desired spatial relationship, said implant defining a hole therethrough;

a first elongated stud defining an engaging surface and having a first portion and an opposite second portion extendable through said hole of said implant;

a foot rigidly attached to said first portion of said stud and projecting outwardly therefrom, said foot being receivable through the opening in the cortical layer of the bone, said foot having an upper surface for contacting the cortical layer when said foot is received through the opening; and a fastener for engaging said engaging surface of said stud, said fastener having a bearing surface for bearing against said implant, said fastener clamping said implant between the bone and said bearing surface of said fastener when said fastener is engaged to said engaging surface of said stud and said upper surface of said foot is contacting the cortical layer.

2. The system of claim 1, wherein said engaging surface is externally threaded and said fastener is internally threaded.

3. The system of claim 2, wherein at least a portion of said second portion defines a hexagonal outer surface disposed opposite said foot to receive a tool to rotate the stud.

4. The system of claim 1 wherein said elongated stud defines a center line and said foot is oriented transverse to said center line.

5. The system of claim 1 wherein said foot is elongated having a length that is greater than a width of said foot.

6. The system of claim 5 wherein said foot includes opposites ends and said center line intersects said foot between said opposite ends of said foot.

7. The system of claim 1 wherein said foot is integrally formed with said first portion of said stud to form a unitary piece.

* * * * *

UNITED STATES PATENT AND TRADEMARK OFFICE

CERTIFICATE OF CORRECTION

PATENT NO. : 6,146,384
DATED : November 14, 2000
INVENTOR(S) : Casey K. Lee, Robert A. Farris, Bradley Coates, Michael C. Sherman It is certified that error appears in the above-identified patent and that said Letters Patent is hereby corrected as shown below:

Title page,
Item [57], line 1, please insert -- Devices -- before "and".

Signed and Sealed this

Nineteenth Day of March, 2002

*Attest:*

JAMES E. ROGAN

*Attesting Officer*

*Director of the United States Patent and Trademark Office*